United States Patent [19]

Tanaka et al.

[11] Patent Number: 4,990,600
[45] Date of Patent: Feb. 5, 1991

[54] AZOAMIDINE COMPOUNDS HAVING A C-ALKYLATED IMIDAZOLINE RING AND SALTS THEREOF

[75] Inventors: Motoaki Tanaka; Tsutomu Miyagawa; Kazuo Shiraki, all of Saitama, Japan

[73] Assignee: Wako Pure Chemical Industries Ltd., Osaka, Japan

[21] Appl. No.: 488,425

[22] Filed: Feb. 27, 1990

Related U.S. Application Data

[63] Continuation of Ser. No. 364,499, Jun. 9, 1989, abandoned, which is a continuation of Ser. No. 85,155, Aug. 14, 1987, abandoned.

[30] Foreign Application Priority Data

Aug. 28, 1986 [JP] Japan ................... 61-202098
May 7, 1987 [JP] Japan ................... 62-110977

[51] Int. Cl.$^5$ ............... C08F 4/04; C07C 245/04
[52] U.S. Cl. ................... 534/751; 526/218.1; 526/193; 526/204; 526/200
[58] Field of Search ........................... 534/751

[56] References Cited

U.S. PATENT DOCUMENTS 3,799,942  3/1974  Boocock et al. ............. 534/751 X
4,569,979  2/1986  Harada et al. ............... 534/751 X Primary Examiner—Floyd D. Higel
Attorney, Agent, or Firm—Cushman, Darby & Cushman

[57] ABSTRACT

Cyclic azoamidine compounds having the formula and salts thereof are disclosed.

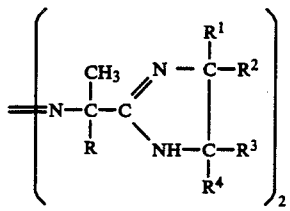

wherein R denotes a methyl group or an ethyl group, and $R^1$, $R^2$, $R^3$ and $R^4$ independently denote a lower alkyl group having one to four carbon atoms or a hydrogen atoms, provided that a case where $R^1$, $R^2$, $R^3$ and $R^4$ are all hydrogen atoms is excluded. The cyclic azoamidine compounds and their salts are useful as polymerization initiators in the production of polymer compounds.

15 Claims, No Drawings

AZOAMIDINE COMPOUNDS HAVING A C-ALKYLATED IMIDAZOLINE RING AND SALTS THEREOF

This is a continuation of application Ser. No. 07/364,499, filed June 9, 1989, which was abandoned upon the filing hereof, which is a continuation of application Ser. No. 07/085,155, filed Aug. 14, 1987, now abandoned.

BACKGROUND OF THE INVENTION

(1) Field of the Invention

The present invention relates to novel cyclic azoamidine compounds and salts thereof which are useful as a polymerization initiator in the production of polymer compounds.

(2) Related Art Statement

Since salts of azoamidine compounds are water-soluble, the azoamidine compounds are compounds useful as a polymerization initiator particularly in aqueous solutions. Among them, salts (hydrochloride, acetates, etc.) of cyclic azoamidine compounds expressed by the following formula are well known as water-soluble polymerization initiators having particularly high polymerization activity.

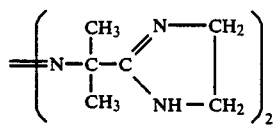

In general, the water-soluble polymerization initiators of this type are used for polymerization of water-soluble monomers such as acrylic acid, acrylamide, allylamine, and vinylpyrolidone, production of cathionic polymers, production of fluoric resins, various emulsion polymerization and photopolymerization, etc. When improvement of polymerization, enhancement of polymerization efficiency, improvement of physical properties, etc. of the polymers in the above uses are considered, appearance of polymerization initiators having higher activity has been strongly desired.

BRIEF SUMMARY OF THE INVENTION

It is an object of the present invention to provide cyclic azoamidine water-soluble polymerization initiators having higher activity as polymerization initiators in the production of polymer compounds.

According to the present invention, there is provided cyclic azoamidine compounds expressed by the following formula [I]:

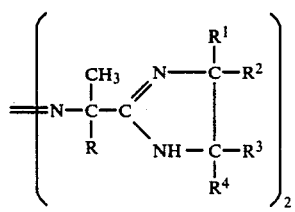

[I]

wherein R denotes a methyl group or an ethyl group, and $R^1, R^2, R^3$ and $R^4$ independently denote a lower alkyl group having from one to four carbon atoms or a hydrogen atom, provided that a case where $R^1, R^2, R^3$ and $R^4$ all denote a hydrogen atom is excluded, or salts thereof.

These and other objects, features and advantages of the present invention will be appreciated upon reading of the following description of the invention, with the understanding that some modifications, variations and changes of the same could be made by the skilled person in the art to which the invention pertains without departing from the spirit of the invention or the scope of claims appended hereto.

DETAILED DESCRIPTION OF THE INVENTION

That is, the cyclic azoamidine compounds according to the present invention are expressed by the formula [I]. In the formula [I], R denotes a methyl group or an ethyl group, and $R^1, R^2, R^3$ and $R^4$ independently denote a lower alkyl group having from one to four carbon atoms, such as a methyl group, an ethyl group, a n-propyl group, an isopropyl group, a n-butyl group, an isobutyl group, a sec-butyl group, a tert-butyl group, or a hydrogen atom, provided that the case where $R^1, R^2, R^3$ and $R^4$ all denote a hydrogen atom is excluded.

As salts of the cyclic azoamidine compounds according to the present invention, mention may be made of, for instance, hydrochlorides, hydrobromides, acetates, etc. of the above cyclic azoamidine compounds.

The azoamidine compounds and the salts thereof according to the present invention are all novel compounds which have not been described in the literatures.

The cyclic azoamidine compounds and the salts thereof according to the present invention can easily be synthesized, for example, in accordance with the following synthesis route.

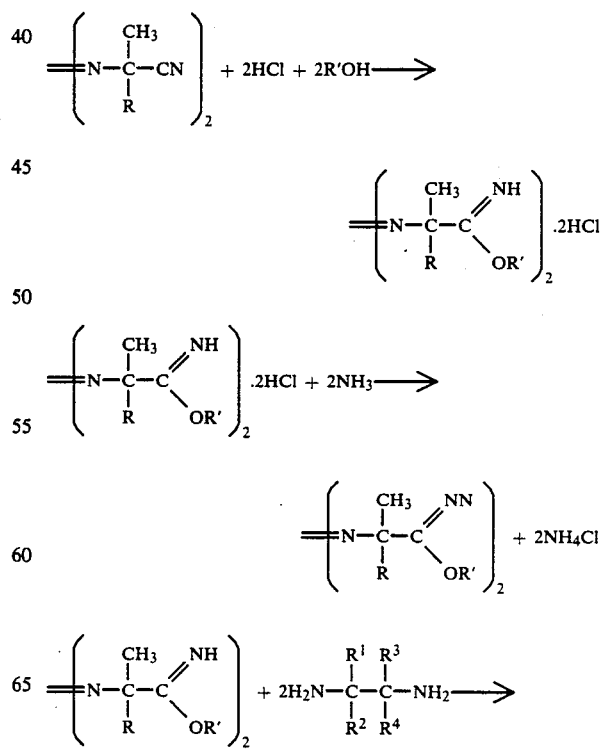

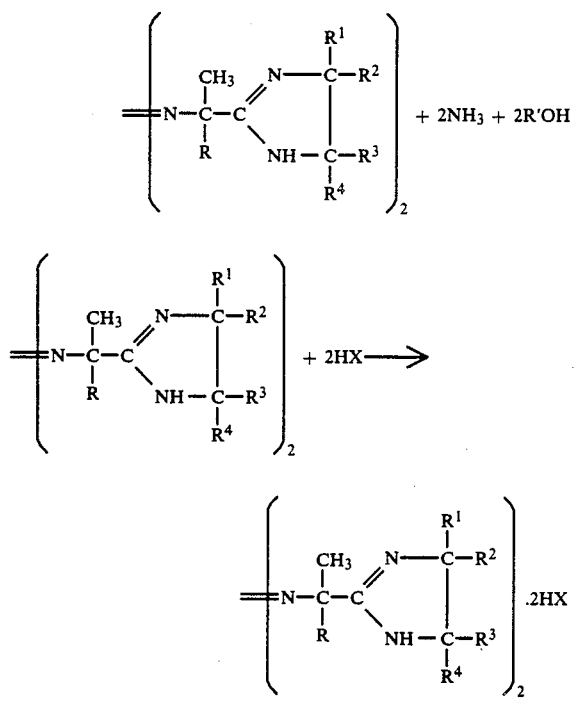

In the above formula, R' denotes a lower alkyl group, and R,R¹,R²,R³ and R⁴ do the same meanings as mentioned above, while HX denotes an inorganic or organic acid such as HCl, HBr, CH₃COOH, etc.

That is, for instance, hydrogen chloride gas and an alcohol are reacted with a corresponding azonitrile as a starting material according to an ordinary method to obtain a hydrochloride of an azoimino ether. Then, the thus obtained hydrochloride is converted to a free azoimino ether through reaction with ammonia gas in an appropriate reaction solvent, and an intended free cyclic azoamidine compound is produced by reacting the resulting free azoimino ether with a corresponding diamine.

A free azoimino ether may be ordinarily reacted with a diamine by contacting the free azoimino ether with a theoretical amount or a slightly excess amount of the diamine relative to the free azoimino ether in a lower alcohol solvent such as methanol or ethanol or in other appropriate organic solvent under the presence of the abovementioned lower alcohol at room temperature of if necessary, under slight cooling for a few hours to several days, using a small amount of acetic acid as a reaction accelerator if necessary. Upon necessity, stirring is arbitrarily performed. After the reaction, the reaction mixture is post-treated in an ordinary manner to isolate a cyclic azoamidine compound.

Further, desired salts of the cyclic azoamidine compounds can be obtained by dissolving the thus obtained free cyclic azoamidine compounds in an appropriate organic solvent capable of dissolving it, for instance, methanol, ethanol, etc., and reacting an arbitrary acid such as an inorganic acid of hydrochloric acid, hydrobromic acid, etc., or an organic acid of acetic acid therewith. Then, the resulting salts may be isolated according to an ordinary technique.

Diamines which are reacted with free azoimino ethers may easily be synthesized according to an ordinary method, for instance, by reacting ammonia with a dihalogen compound, reducing a dinitrile, a dioxyme, an aminonitrile, etc., or producing them from a dicarboxylic acid amide through Hofmann rearrangement, and the thus synthesized diamines may be used.

In the following, examples of the present invention will be shown, but the invention will never be restricted by these examples.

EXAMPLE 1

6 ml of methanol and 14.8 g of 1,2-diaminopropane were added to 100 ml of a toluene solution containing 21.0 g of free 2,2' azobis(1-imino-2-methylpropylmethyl ether), which was subjected to reaction under stirring at room temperature for 7 hours. After the reaction mixture was left for two days, it was concentrated, thereby obtaining 24.3 g of light yellow crystals of a free cyclic azoamidine compound of the following formula:

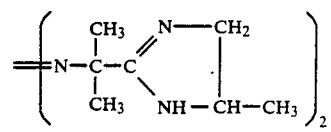

¹HNMR(CDCl₃) δppm: 1.17(6H,d,—CH—C$\underline{H}_3$ × 2), 1.47(12H,s,=N—C(CH₃)(CH₃)— × 2), 3.0–3.6(2H,m,—C$\underline{H}$—CH₃ × 2), 3.80(4H,d,—CH₂— × 2), 5.40(2H,broad,—NH— × 2).

UV: $\lambda_{max}$ 365nm ($\epsilon$25.5/H₂O).

15 g of this free azoamidine compound was dissolved into 150 ml of methanol, into which 4.0 g of hydrogen chloride gas was fed to react them. After concentrating to dryness, the reaction mixture was dissolved into 70 ml of methanol, and then subjected to crystallization with addition of 180 ml of acetone. 17 g of white crystals of a hydrochloride (dihydrochloride) of the free cyclic azoamidine compound was obtained through filtration and drying.

mp 156.5°–158° C. (dec).

¹HNMR(CD₃OD) δppm: 1.43(6H,d,—CH—C$\underline{H}_3$ × 2), 1.60(12H,s,=N—C(CH₃)(CH₃)— × 2), 3.0–3.8(2H,m,—C$\underline{H}$—CH₃ × 2), 4.2(4H,d,—CH₂— × 2).

UV: $\lambda_{max}$ 362nm ($\epsilon$25.2/H₂O).

EXAMPLE 2

23.8 g of light yellow crystals of an intended free cyclic azoamidine compound having the following formula was obtained in the same manner as in Example 1 except that 17.7 g of 1,2-diamino-2-methylpropane was used instead of 14.8 g of 1,2-diaminopropane.

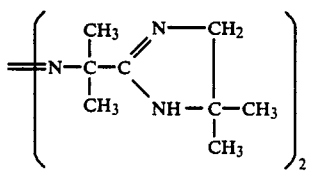

mp 96.0°–98.0° C. (dec).

$^1$HNMR(CDCl$_3$) δppm: 1.27(12H,s,—NH—C(CH$_3$)—CH$_3$ × 2), 1.47(12H,s,=N—C(CH$_3$)(CH$_3$)— × 2), 3.40(4H,s,—CH$_2$— × 2), 5.38(2H,broad,—NH— × 2).

UV: λ$_{max}$ 368nm (ε24.3/H$_2$O).

Hydrogen chloride gas was introduced into a methanol solution containing 15 g of this free cyclic azoamidine compound in the same manner as in Example 1, which was treated in the same manner as in Example 1 to obtain 17.9 g of white crystals of a hydrochloride (dihydrochloride) of the free azoamidine compound. mp 110°–112° C. (dec).

$^1$HNMR(CD$_3$OD) δppm: 1.50(12H,s,—NH—C(CH$_3$)—CH$_3$ × 2), 1.60(12H,s,=N—C(CH$_3$)(CH$_3$)— × 2), 3.76(4H,s,—CH$_2$— × 2).

UV: λ$_{max}$ 362nm (ε23.4/H$_2$O).

EXAMPLE 3

8.4 g of free 2,2'-azobis(1-imino-2-methylpropyl-methyl ether), 0.15 ml of acetic acid and 3 ml of methanol were dissolved into 40 ml of toluene, and 7.1 g of 2,3-diaminobutane was added thereto. Then, the reaction was carried out under stirring at room temperature for 13 hours. After being left for 6 days, the reaction solution was concentrated, thereby obtaining 10.8 g of light yellow crystals of an intended free cyclic azoamidine compound of the following formula:

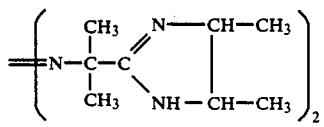

The crystals were dissolved into 100 ml of methanol, into which 3 g of hydrogen chloride gas was introduced for reacting them. After concentrating to dryness, the reaction product was crystallized by adding 100 ml of acetone, followed by filtration and drying to obtain 8.8 g of light yellowish white crystals of a hydrochloride (dihydrochloride) of the free azoamidine compound. mp 166.5° C. (dec).

$^1$HNMR(CD$_3$OD) δppm: 1.30(6H,d,—NH—CH(CH$_3$)—CH$_3$ × 2), 1.39(6H,d,=N—CH(CH$_3$)—CH$_3$ × 2), 1.60(12H,s,=N—C(CH$_3$)(CH$_3$)— × 2), 4.00(2H,—NH—CH(CH$_3$)—CH$_3$ × 2), 4.50(2H,=N—CH(CH$_3$)—CH$_3$ × 2).

UV: λ$_{max}$ 368nm (ε26.4/H$_2$O).

EXAMPLE 4

7.9 g of free 2,2'-azobis(1-imino-2-methylpropyl-methyl ether), 0.1 ml of acetic acid and 1.8 ml of methanol were dissolved into 40 ml of toluene, and 7.5 g of 2,3-diaminopentane was added thereto. Then, the reaction was carried out under stirring at room temperature for 12.5 hours. After being left for 6 days, the reaction solution was concentrated, thereby obtaining 12.4 g of light yellow crystals of an intended free cyclic azoamidine compound of the following formula:

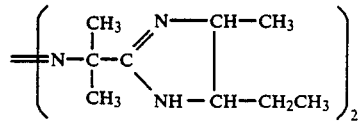

The crystals were dissolved into 100 ml of methanol, to which 2.7 g of hydrogen chloride gas was introduced for reacting them. After concentrating to dryness, the reaction product was dissolved into 30 ml of methanol, to which 120 ml of acetone was added to effect crystallization, the same procedure is repeated again, followed by filtration and drying, thereby obtaining 8.4 g of light yellowish white crystals of a hydrochloride (dihydrochloride) of the free azoamidine compound. mp 136.4° C. (dec).

$^1$HNMR(CD$_3$OD) δppm:

1.00, 1.06(6H,t,—NH—CH(CH$_2$CH$_3$)— × 2), 1.36, 1.42(6H,d,=N—CH(CH$_3$)— × 2), 1.60(12H,s,=N—C(CH$_3$)(CH$_3$)— × 2), 1.30–2.0(4H,m,—NH—CH(CH$_2$CH$_3$)— × 2), 4.03(2H,q,—NH—CH(CH$_2$CH$_3$)— × 2), $$4.50(2H, m, =N-C\underline{H}-CH_3 \times 2).$$

UV: $\lambda_{max}$ 362nm ($\epsilon$27.5/H$_2$O).

EXAMPLE 5

3.8 g of free 2,2'-azobis(1-imino-2-methylpropylmethyl ether), 0.1 ml of acetic acid and 0.1 ml of methanol were dissolved into 18 ml of toluene, to which 4.7 g of 5-methyl-2,3-diaminohexane was added. Then, the reaction was carried out under stirring at 30° C. for 36 hours. The reaction solution was concentrated, thereby obtaining 6.2 g of light yellow crystals of an intended free cyclic azoamidine compound of the following formula:

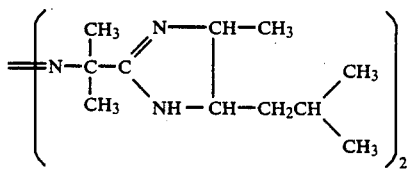

This free cyclic azoamidine compound was dissolved into 40 ml of methanol, to which 5 ml of a 30% methanol solution of hydrogen chloride was added to react them. After concentrating to dryness, 100ml of acetone was added to effect crystallization, followed by filtration and drying to obtain 3.2 g of light yellowish white crystals of a hydrochloride (dihydrochloride) of the free cyclic azoamidine compound.

mp 120.8° C. (dec).

$^1$HNMR(CD$_3$OD) $\delta$ppm:

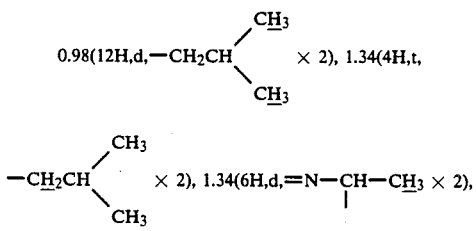

$$1.60(12H, s, =N-\underset{\underset{C\underline{H}_3}{|}}{\overset{\overset{CH_3}{|}}{C}}- \times 2),$$

$$1.5-2.0(2H, m, -CH_2C\underline{H}\diagup^{CH_3}_{\diagdown CH_3} \times 2),$$

$$3.85-4.20(2H, m, =N-C\underline{H}-CH_3 \times 2),$$

$$4.20-4.70(2H, m, -NH-C\underline{H}-CH_2CH \times 2).$$

UV: $\lambda_{max}$ 362nm ($\epsilon$27.9/H$_2$O).

EXAMPLE 6

15.4 g of free 2,2'-azobis(1-imino-2-methylbutylmethyl ether), 0.3 ml of acetic acid and 6 ml of methanol were dissolved into 100 ml of toluene, to which 10.5 g of 2-methyl-1,2-diaminopropane was added. Then, the reaction was carried out under stirring at room temperature for 7 hours. After being left for two days, the reaction solution was concentrated to obtain 34.2 g of light yellow crystals of an intended free cyclic azoamidine compound of the following formula:

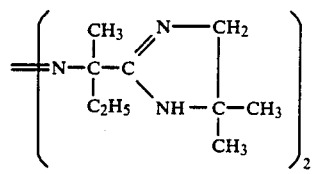

The thus obtained product was dissolved into 70 ml of methanol, to which 5 g of hydrogen chloride gas was introduced to effect the reaction. After being concentrating to dryness, the resulting reaction product was dissolved into 100 ml of methanol again, to which 200 ml of acetone was added to effect crystallization, the same procedure repeated again, followed by filtration and drying, thereby obtaining 5.8 g of a hydrochloride (dihydrochloride) of the free cyclic azoamidine compound.

mp 137.5° C. (dec).

$$^1\text{HNMR(CD}_3\text{OD)} \delta\text{ppm: } 1.83(6H, t, =N-\underset{\underset{C\underline{H}_2-CH_3}{|}}{\overset{|}{C}}- \times 2),$$

$$1.50(18H, s, -CH_3 \times 6), 2.01(4H, q, =N-\underset{\underset{C\underline{H}_2-CH_3}{|}}{\overset{|}{C}} \times 2),$$

$$3.80(4H, s, =N-C\underline{H}_2 \times 2).$$

UV: $\lambda_{max}$ 368nm ($\epsilon$23.5/H$_2$O).

EXAMPLE 7

1 ml of methanol, 0.1 ml of acetic acid and 4.5 g of 2-methyl-1,2-diaminobutane were added to 23 ml of a toluene solution containing 4.8 g of free 2,2'-azobis(1-imino-2-methylpropylmethyl ether), which was subjected to the reaction at room temperature for 10 hours. After the reaction, the reaction mixture was left for two days. Then, the reaction solution was concentrated to obtain 7.7 g of light yellow powdery crystals of an intended free cyclic azoamidine compound of the following formula:

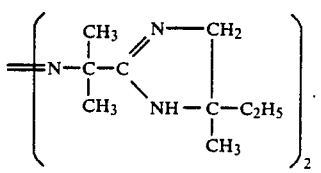

The thus obtained product was converted to a hydrochloride thereof according to the method of Example 6, thereby obtaining 7.4 g of the hydrochloride (dihydrochloride) of the free cyclic azoamidine compound.
mp 125.5°-130° C. (dec).

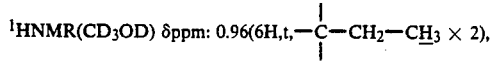

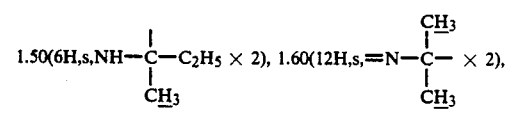

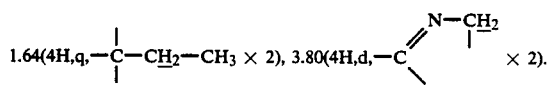

UV: $\lambda_{max}$ 362nm ($\epsilon$23.5/H$_2$O).

EXAMPLE 8

5.6 g of light yellow powdery crystals of a hydrochloride (dihydrochloride) of an intended cyclic azoamidine compound was obtained by the same reaction and post-treatment as in Example 7 except that 8.0 g of 2,4-dimethyl-1,2-diaminopentane was used instead of 4.5 g of 2-methyl-1,2-diaminobutane.

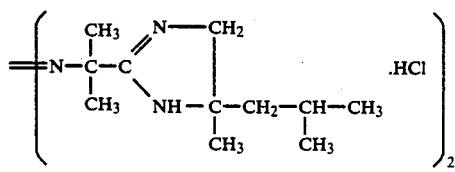

mp 94.0° C. (dec).

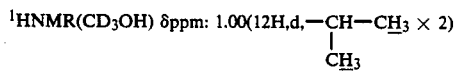

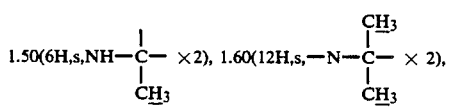

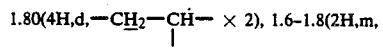

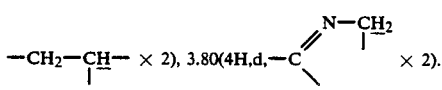

UV: $\lambda_{max}$ 362.5nm ($\epsilon$28.4/H$_2$O).

EXAMPLE 9

3.8 g of free 2,2'-azobis(1-imino-2-methylpropyl-methyl ether), 0.1 ml of acetic acid and 1 ml of methanol were dissolved into 18 ml of toluene, to which 4.1 g of 4-methyl-2,3-diaminopentane was added. Then, the reaction was carried out under stirring at 30 ° C for 31 hours. Thereafter, the reaction solution was concentrated to obtain 6.3 g of a light yellow liquid of an intended free cyclic azoamidine compound of the following formula:

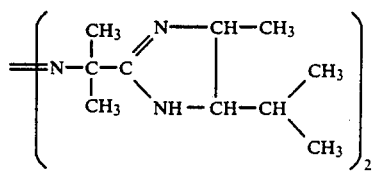

This reaction product was dissolved into 40 ml of methanol, to which 6 ml of a 30% methanol solution of hydrogen chloride to react them. After concentrating to dryness, 50 ml of acetone was added to effect crystallization, followed by filtration and drying, thereby obtaining 3.7 g of light yellowish white crystals of a hydrochloride (dihydrochloride) of the free cyclic azoamidine compound.
mp 139° C.—(dec).

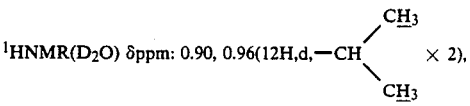

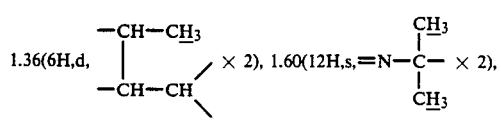

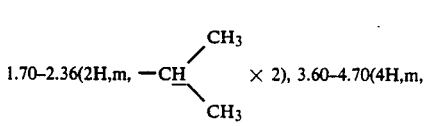

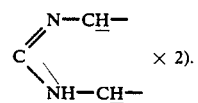

UV: $\lambda_{max}$ 363nm ($\epsilon$27.1/H$_2$O).

EXAMPLE 10

8.8 g of free 2,2'-azobis(1-imino-2-methylpropyl-methyl ether), 0.3 ml of acetic acid and 3 ml of methanol were dissolved into 42 ml of toluene, to which 12.0 g of 3,4-diaminoheptane was added. Then, the reaction was carried out under stirring at 30° C. for 7 days. Thereafter, the reaction solution was concentrated, thereby obtaining 14.8 g of a light yellow liquid of an intended free cyclic azoamidine compound of the following formula:

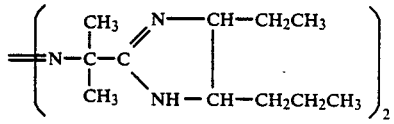

The thus obtained liquid was dissolved into 50 ml of methanol, to which 3.5 g of hydrogen chloride gas was introduced to react them. After concentrating to dryness, 100 ml of a 8% methanol-acetone solution was added to effect crystallization, followed by filtration and drying, thereby obtaining 4.1 g of a hydrochloride (dihydrochloride) of the free hydrochloride.
mp 137.0°-138.5° C. (dec).

$^1$HNMR(CD$_3$OD) δppm: 0.68–1.33(12H,m,

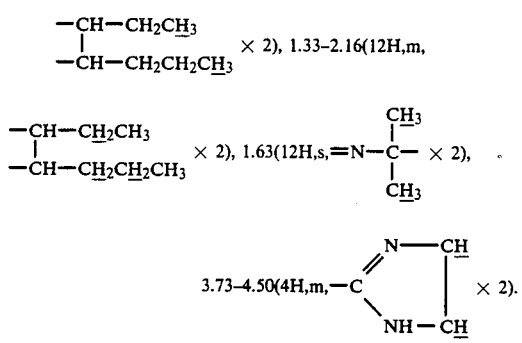
× 2), 1.33–2.16(12H,m, 1.63(12H,s,=N—C(CH$_3$)$_2$— × 2), 3.73–4.50(4H,m, —C(=N—CH)(NH—CH) × 2).

UV: λ$_{max}$ 362nm (ε29.4/H$_2$O).

EXAMPLE 11

8.9 g of free 2,2'-azobis(1-imino-2-methylpropyl-methyl ether), 0.3 ml of acetic acid, and 3 ml of methanol were dissolved into 42 ml of toluene, to which 14.0 g of 4,5-diaminononane was added. Then, the reaction was carried out under stirring at 30° C. for 7 days. The reaction solution was concentrated, thereby obtaining 15.5 g of a light yellow liquid of an intended free cyclic azoamidine compound of the following formula:

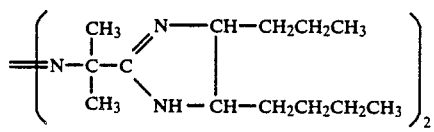

This liquid was dissolved into 50 ml of methanol, to which 14 ml of a 30% methanol solution of hydrogen chloride was added to react them. After concentrating to dryness, 150 ml of acetone was added to effect crystallization, followed by filtration and drying, thereby obtaining 3.4 g of crystals of a hydrochloride (dihydrochloride) of the free cyclic azoamidine compound.

mp 129.3° C.—(dec).

$^1$HNMR(CD$_3$OD) δppm: 0.73–1.20(12H,m,

—CH(—CH$_2$CH$_2$CH$_3$)(—CH$_2$CH$_2$CH$_2$CH$_3$) × 2), 1.20–2.00(20H,m,

—CH(—CH$_2$CH$_2$CH$_3$)(—CH$_2$CH$_2$CH$_2$CH$_3$) × 2), 1.63(12H,s,

=N—C(CH$_3$)$_2$— × 2), 3.80–4.50(4H,m, —C(=N—CH)(NH—CH) × 2).

UV: λ$_{max}$ 360nm (ε30.2/H$_2$O).

EXAMPLE 12

9.5 g of free 2,2'-azobis(1-imino-2-methylbutylmethyl ether), 0.3 ml of acetic acid and 3 ml of methanol were dissolved into 80 ml of toluene, to which 7.0 g of 2,3-diaminobutane was added. Then, the reaction was carried out under stirring at room temperature for 7 days. Thereafter, the reaction solution was concentrated, thereby obtaining 14.3 g of light yellow crystals of an intended free cyclic azoamidine compound of the following formula:

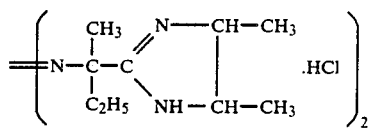

The thus obtained crystals were dissolved into 100 ml of methanol, to which 3 g of hydrogen chloride gas was introduced to react them. After concentrating to dryness, 120 ml of a 20% methanol-acetone solution was added to effect crystallization, followed by filtration and drying, thereby obtaining 4.2 g of light yellowish white crystals of a hydrochloride (dehydrochloride) of the free cyclic azoamidine compound.

mp 160.0° C. (dec).

$^1$HNMR(CD$_3$OD) δppm: 0.86, 0.89(16H,t,

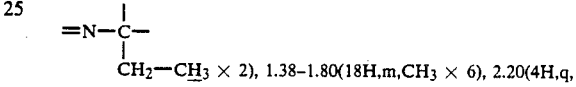
× 2), 1.38–1.80(18H,m,CH$_3$ × 6), 2.20(4H,q,

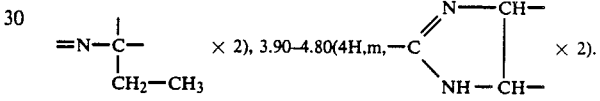
× 2), 3.90–4.80(4H,m, —C(=N—CH)(NH—CH) × 2).

UV: λ$_{max}$ 370nm (ε25.4/H$_2$O).

Rate constants of decomposition were measured by using 1% aqueous solutions each containing the hydrochlorides of the cyclic azoamidine compounds according to the present invention obtained in Example 1 to 12 and a hydrochloride of a known cyclic azoamidine compound (Comparative Example) of the following formula:

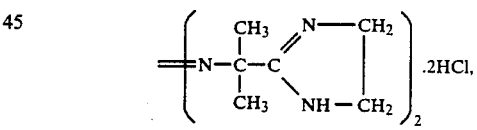

TABLE 1

| Example | Rate constants of decomposition of cyclic azoamidine compound 50° C. | (sec$^{-1}$) 60° C. |
|---|---|---|
| 1 | 6.73 × 10$^{-5}$ | 2.53 × 10$^{-4}$ |
| 2 | 9.30 × 10$^{-5}$ | 3.44 × 10$^{-4}$ |
| 3 | 8.94 × 10$^{-5}$ | 3.45 × 10$^{-4}$ |
| 4 | 1.10 × 10$^{-4}$ | 4.20 × 10$^{-4}$ |
| 5 | 9.78 × 10$^{-5}$ | 3.66 × 10$^{-4}$ |
| 6 | 4.47 × 10$^{-5}$ | 1.67 × 10$^{-4}$ |
| 7 | 7.38 × 10$^{-5}$ | 2.89 × 10$^{-4}$ |
| 8 | 7.08 × 10$^{-5}$ | 2.76 × 10$^{-4}$ |
| 9 | 1.01 × 10$^{-4}$ | 3.67 × 10$^{-4}$ |
| 10 | 1.41 × 10$^{-4}$ | 5.39 × 10$^{-4}$ |
| 11 | 1.31 × 10$^{-4}$ | 5.27 × 10$^{-4}$ |
| 12 | 5.05 × 10$^{-5}$ | 1.83 × 10$^{-4}$ |
| Comparative | 4.02 × 10$^{-5}$ | 1.35 × 10$^{-4}$ |

TABLE 1-continued

| Example | Rate constants of decomposition of cyclic azoamidine compound (sec$^{-1}$) 50° C. | 60° C. |
|---|---|---|
| Example | | |

As obvious from Table 1, the rate constants of decomposition of all the compounds according to the present invention are far greater as compared with that of the known cyclic azoamidine compound. Thus, it can be understood that polymerization activity of the former is conspicuously higher than that of the latter.

The present invention is to provide novel polymerization initiators in the production of polymer compounds. The cyclic azoamidine polymerization initiators according to the present invention exhibit a remarkable effect in that their polymerization activity is far higher as compared with that of known cyclic azoamidine compounds.

What is claimed is:

1. A cyclic azoamidine compound having the formula:

$$\left\{ =N-\underset{R}{\overset{CH_3}{\underset{|}{C}}}-C\underset{NH-\underset{R^4}{\overset{R^3}{\underset{|}{C}}-R^3}}{\overset{N=\underset{|}{\overset{R^1}{C}-R^2}}{\diagup}} \right\}_2$$

wherein R represents methyl or ethyl and any one of each of any two of R$^1$, R$^2$, R$^3$ and R$^4$ represents lower alkyl having one to four carbon atoms while each of the rest represents hydrogen, or a salt thereof.

2. A cyclic azoamidine compound to claim 1, wherein the salt of the cyclic azoamidine compound is a salt selected from the group consisting of a hydrochloride, a hydrobromide and an acetate.

3. A cyclic azoamidine compound according to claim 1, expressed by the following formula:

$$\left\{ =N-\underset{CH_3}{\overset{CH_3}{\underset{|}{C}}}-C\underset{NH-CH-CH_3}{\overset{N-CH_2}{\diagup}} \right\}_2$$

or a salt thereof.

4. A cyclic azoamidine compound according to claim 1, expressed by the following formula:

$$\left\{ =N-\underset{CH_3}{\overset{CH_3}{\underset{|}{C}}}-C\underset{NH-\underset{CH_3}{\overset{CH_3}{\underset{|}{C}-CH_3}}}{\overset{N-CH_2}{\diagup}} \right\}_2$$

or a salt thereof.

5. A cyclic azoamidine compound according to claim 1, expressed by the following formula:

$$\left\{ =N-\underset{CH_3}{\overset{CH_3}{\underset{|}{C}}}-C\underset{NH-CH-CH_3}{\overset{N-CH-CH_3}{\diagup}} \right\}_2$$

or a salt thereof.

6. A cyclic azoamidine compound according to 1, expressed by the following formula:

$$\left\{ =N-\underset{CH_3}{\overset{CH_3}{\underset{|}{C}}}-C\underset{NH-CH-CH_2CH_3}{\overset{N-CH-CH_3}{\diagup}} \right\}_2$$

or a salt thereof.

7. A cyclic azoamidine compound according to claim 1, expressed by the following formula:

$$\left\{ =N-\underset{CH_3}{\overset{CH_3}{\underset{|}{C}}}-C\underset{NH-CH-CH_2CH\underset{CH_3}{\overset{CH_3}{\diagdown}}}{\overset{N-CH-CH_3}{\diagup}} \right\}_2$$

or a salt thereof.

8. A cyclic azoamidine compound according to claim 1, expressed by the following formula:

$$\left\{ =N-\underset{C_2H_5}{\overset{CH_3}{\underset{|}{C}}}-C\underset{NH-\underset{CH_3}{\overset{|}{C}-CH_3}}{\overset{N-CH_2}{\diagup}} \right\}_2$$

or a salt thereof.

9. A cyclic azoamidine compound according to claim 1, expressed by the following formula:

$$\left\{ =N-\underset{CH_3}{\overset{CH_3}{\underset{|}{C}}}-C\underset{NH-\underset{CH_3}{\overset{|}{C}-C_2H_5}}{\overset{N-CH_2}{\diagup}} \right\}_2$$

or a salt thereof.

10. A cyclic azoamidine compound according to claim 1, expressed by the following formula:

$$\left\{ =N-\underset{CH_3}{\overset{CH_3}{\underset{|}{C}}}-C\underset{NH-\underset{CH_3}{\overset{|}{C}}-CH_2-\underset{CH_3}{\overset{|}{CH}}-CH_3}{\overset{N-CH_2}{\diagup}} \right\}_2 \cdot HCl$$

or a salt thereof.

11. A cyclic azoamidine compound according to claim 1, expressed by the following formula:

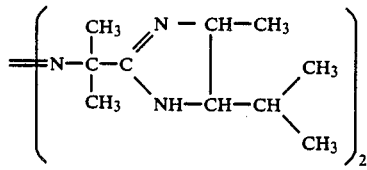

or a salt thereof.

12. A cyclic azoamidine compound according to claim 1, expressed by the following formula:

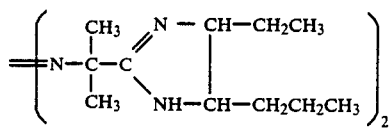

or a salt thereof.

13. A cyclic azoamidine compound according to claim 1, expressed by the following formula:

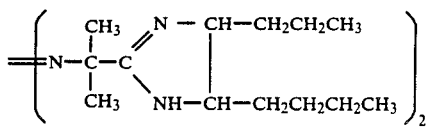

or a salt thereof.

14. A cyclic azoamidine compound according to claim 1, expressed by the following formula:

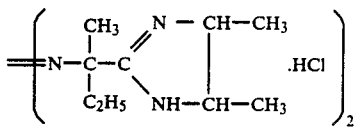

or a salt thereof

15. A cyclic azoamidine compound according to claim 1 having the formula:

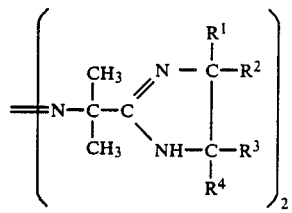

wherein any one or each of any two of $R^1$, $R^2$, $R^3$ and $R^4$ represents a lower alkyl having one to four carbon atoms while each of the rest represents hydrogen, or a salt thereof.

* * * * *